(12) United States Patent
Gantz et al.

(10) Patent No.: US 7,847,106 B2
(45) Date of Patent: Dec. 7, 2010

(54) PROCESS FOR THE PREPARATION OF MACROCYCLIC COMPOUNDS

(75) Inventors: Francois Gantz, Rixheim (FR); Helmut Stahr, Loerrach (DE)

(73) Assignee: Roche Palo Alto LLC, Palo Alto, CA (US)

( * ) Notice: Subject to any disclaimer, the term of this patent is extended or adjusted under 35 U.S.C. 154(b) by 210 days.

(21) Appl. No.: 12/150,029

(22) Filed: Apr. 24, 2008

(65) Prior Publication Data
US 2008/0269502 A1    Oct. 30, 2008

(30) Foreign Application Priority Data
Apr. 24, 2007  (EP)  .................. 07106771

(51) Int. Cl.
*C07D 209/44*  (2006.01)
(52) U.S. Cl. ..................................... 548/465
(58) Field of Classification Search .................. 548/465
See application file for complete search history.

(56) References Cited

U.S. PATENT DOCUMENTS

2008/0039375 A1* 2/2008 Moore et al. .................. 514/9

FOREIGN PATENT DOCUMENTS

| WO | WO 2005/037214 A2 | 4/2005 |
| WO | WO 2005/037214 A3 | 4/2005 |
| WO | WO 2008/005511 A2 | 1/2008 |

* cited by examiner

*Primary Examiner*—Shawquia Young
(74) *Attorney, Agent, or Firm*—Brian L. Buckwalter

(57) ABSTRACT

The present invention relates to a new process for the preparation of tripeptides of formula I

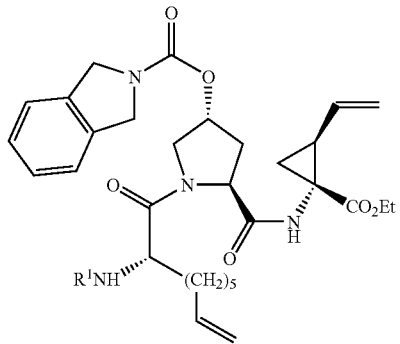

wherein $R^1$ is an amino protecting group and X is a halogen atom and wherein the tipeptide contains two olefinic moieties suitably disposed to undergo an intramolecular olefin metathesis reaction and produce macrocyclic tripeptides useful for the manufacture of macrocyclic HCV protease inhibitors.

9 Claims, No Drawings

PROCESS FOR THE PREPARATION OF MACROCYCLIC COMPOUNDS

CROSS REFERENCE TO PRIOR APPLICATIONS

This application claims the benefit of priority to EP 07106771.4 filed Apr. 24, 2007 the contents of which are hereby incorporated in their entirety by reference.

FIELD OF THE INVENTION

The present invention relates to an improved process for the preparation of tripeptide dienes which are useful intermediates for the preparation of macrocyclic tripeptides that inhibit the HCV protease. The present invention provides an improved process which is applicable on commercial scale and delivers the diene of formula I in high quality and yield.

BACKGROUND OF THE INVENTION

Compounds of formula VII have been disclosed to be potent inhibitors of HCV protease useful in treatment on patients infected with HCV. A particularly useful intermediate is a

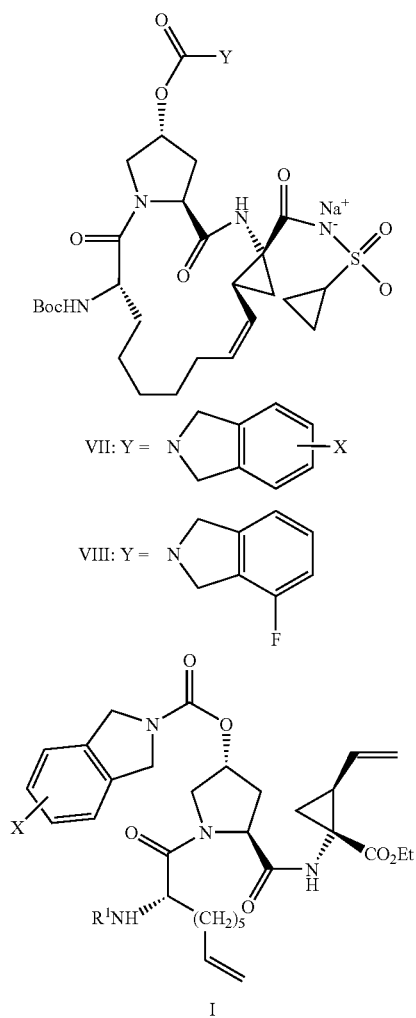

compound of formula VIII. Dienes of formula I wherein $R^1$ is an amino protecting group and X is a halogen atom are useful intermediates for the manufacture of macrocyclic HCV protease inhibitors of the formula VII and VIII.

The known processes for the preparation of the diene compound of the formula I suffer from unstable intermediates, lack of purification steps, the use of corrosive reagents and intermediates, and hazardous and expensive coupling reagents (PCT Publication WO 2005/037214). Therefore the known process is not suitable for large scale production.

SUMMARY OF THE INVENTION

The present invention provides an improved process for the preparation of a compound of formula I by coupling dipeptide V and an N-protected amino acid of formula VIa wherein $R^1$ is an

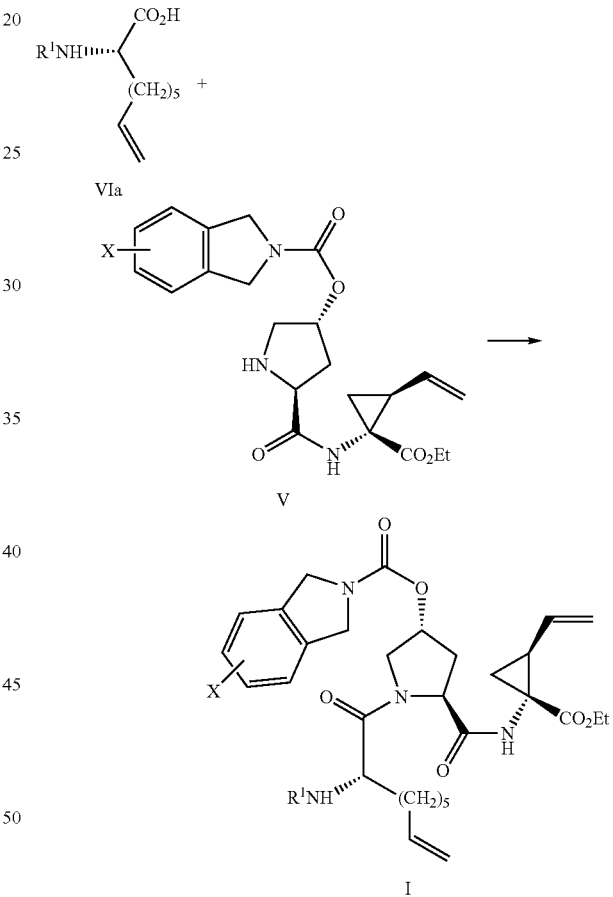

amino protecting group and X is a halogen atom comprising the coupling the carboxylic acid of formula VIa and the dipeptide V. The invention further provides improved methods for preparing compounds of formula V.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The following definitions are set forth to illustrate and define the meaning and scope of the various terms used to describe the invention herein.

The term "amino protecting group" refers to any substituents conventionally used to hinder the reactivity of the amino group. Suitable amino protecting groups are described in Green T., "Protective Groups in Organic Synthesis", Chapter 7, John Wiley and Sons, Inc., 1991, 309-385. Suitable amino protecting groups are Fmoc, Cbz, Moz, Boc, Troc, Teoc or Voc. A preferred amino protecting group, as defined in $R^1$ and $R^2$, is Boc.

The coupling reaction as a rule is performed according to methods known in the art for peptide synthesis (e.g. Houben Weyl "Synthesis of Peptides and Peptidomimetics", Chapter 3, Thieme Stuttgart New York, 2004, 425-588)

The coupling reaction requires a coupling agent. Typical coupling agents which have proved useful include (i) alkyl chloroformates such as methyl-, ethyl-, isopropyl-, sec-butyl, isobutyl- and cyclopentylchloroformate, (ii) carboxylic acid halogenides such as pivaloylchloride, from carbodiimides such as DCC, diisopropylcarbodiimide and EDCI. Also TBTU or 2-chloro-4,6-dimethoxy-1,3,5-triazine (CDMT) can be used as coupling agent. The carbodiimides may be used together with additives such as with HOBt or N-hydroxysuccinimide. Preferred coupling agents are isobutylchloroformate or pivaloylchloride.

The term "halogen" refers to fluorine, chlorine, bromine and iodine. The preferred definition for X is fluorine.

The term "polar aprotic solvent" means organic solvents such as formamide, N,N-dimethylformamide, dimethylsulfoxide, N-methylpyrrolidone or hexamthylphosphoramide.

The term "polar protic solvent" means organic solvents such as lower alkanols, formic acid and acetic acid.

In one embodiment of the present invention there is provide a process for preparing a compound of formula I as depicted in SCHEME A wherein $R^1$ is an amino protecting group and X is a halogen atom comprising the coupling the carboxylic acid of formula VIa and the dipeptide V. In a second embodiment of the present invention there is provided a process for preparing a compound of formula I wherein $R^1$ is an amino protecting group and X is a halogen atom comprising the coupling the carboxylic acid of formula VIa and the dipeptide V utilizing a coupling agent selected from the group consisting of alkyl chloroformates, carboxylic acid halogenides and carbodiimides in the presence of a tertiary amine.

In a third embodiment of the present invention there is provided a process for preparing a compound of formula I wherein $R^1$ is an amino protecting group and X is a halogen atom comprising the coupling the carboxylic acid of formula VIa and the dipeptide V utilizing isobutyl choroformate or pivaloyl chloride as the coupling agent and NMM or TEA as the tertiary amine.

In a fourth embodiment of the present invention there is provide a process for preparing a compound of formula I wherein $R^1$ is an amino protecting group and X is a fluorine comprising the coupling the carboxylic acid of formula VIa and the dipeptide V.

In a fifth embodiment of the present invention there is provided a process for preparing a compound of formula I wherein $R^1$ is an amino protecting group and X is a halogen atom

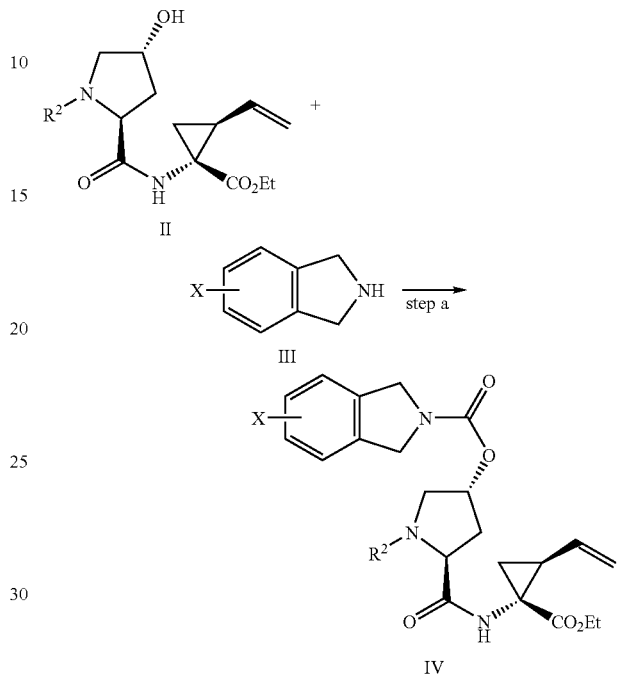

SCHEME B comprising the steps of: (a) reacting a dipeptide of formula II wherein $R^2$ is an amino protecting group with CDI and a compound according to formula III wherein X is a halogen and III is a free base or a salt thereof to form an N-protected carbamate of the formula IV; (b) deprotecting the

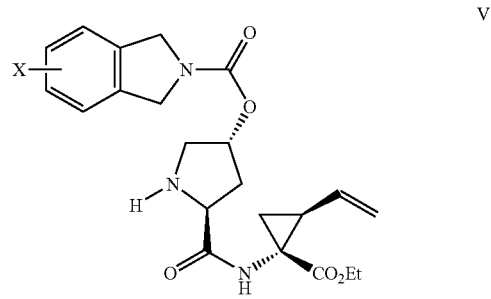

N-protected carbamate to form a compound of formula V wherein X is as above; and (c) coupling the carbamate of formula V with the carboxylic acid of formula VIa or with a salt thereof to form a tripeptide of formula I.

In a sixth embodiment of the present invention there is provided a process provided a process for preparing a compound of formula I wherein $R^1$ is a Boc protecting group and X is a fluorine atom comprising the steps of: (a) reacting a dipeptide of formula II wherein $R^2$ is a Boc protecting group with CDI and a compound according to formula III wherein X is a fluorine atom and III is a free base or a salt thereof to form an N-protected carbamate of the formula IV; (b) deprotecting the N-protected carbamate to form a compound of formula V wherein X is a fluorine atom; and (c) coupling the carbamate of formula V wherein X is fluorine with the carboxylic acid of formula VIa wherein R¹ is a Boc group or with a salt thereof to form a tripeptide of formula I.

In a seventh embodiment of the present invention there is provided a process for preparing na compound of formula Ib comprising the steps of: (a) reacting a dipeptide of formula II wherein R² is an amino protecting group with CDI and a compound according to formula IIIa wherein

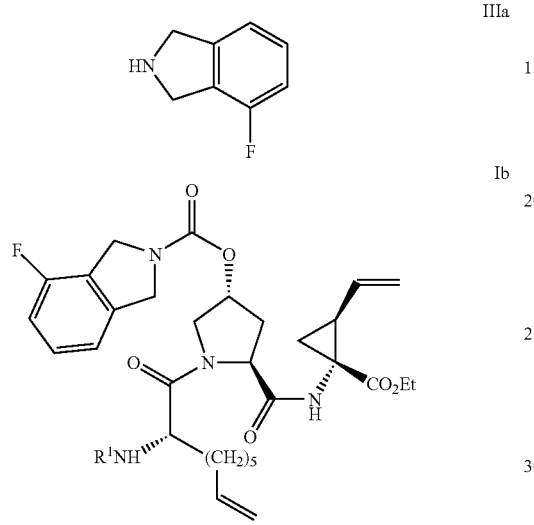

X is a halogen and III is a free base or a salt thereof to form an N-protected carbamate of the formula IV; (b) deprotecting the N-protected carbamate.

In a eighth embodiment of the present invention there is provided a process for preparing a compound of formula I wherein R¹ is an amino protecting group and X is a halogen atom comprising the steps of: (a) reacting a dipeptide of formula II wherein R² is an amino protecting group with CDI and a compound according to formula III wherein X is a halogen and III is a free base or a salt thereof to form an N-protected carbamate of the formula in the presence of a tertiary amine base; (b) deprotecting the N-protected carbamate to form a compound of formula V wherein X is as above; and (c) coupling the carbamate of formula V with the carboxylic acid of formula VIa or with a salt thereof to form a tripeptide of formula I.

In a ninth embodiment of the present invention there is provided a process provided a process for preparing a compound of formula I wherein R¹ is a Boc protecting group and X is a fluorine atom comprising the steps of: (a) reacting a dipeptide of formula II wherein R² is a Boc protecting group with CDI and a compound according to formula III wherein X is a fluorine atom and III is a free base or a salt thereof to form an N-protected carbamate of the formula IV; (b) deprotecting the N-protected carbamate with an acid in an organic solvent to form a compound of formula V wherein X is a fluorine atom; and (c) coupling the carbamate of formula V wherein X is fluorine with the carboxylic acid of formula VIa wherein R¹ is a Boc group or with a salt thereof to form a tripeptide of formula I.

In a tenth embodiment of the present invention there is provided a compound according to formula IV useful in the preparation of compounds according to formula I.

In an eleventh of the present invention there is provided a compound according to formula V useful in the preparation of compounds according to formula I.

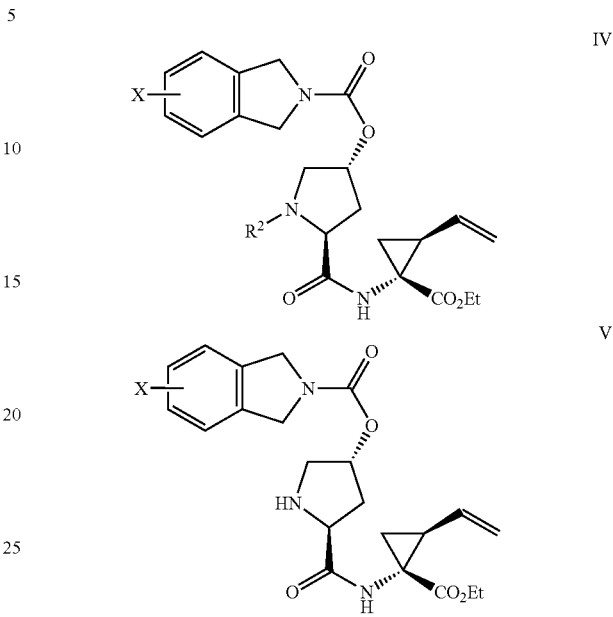

The dipeptide of formula II which is the starting compound of the process of the present invention can be obtained by applying procedures known in the art. A possible approach is outlined

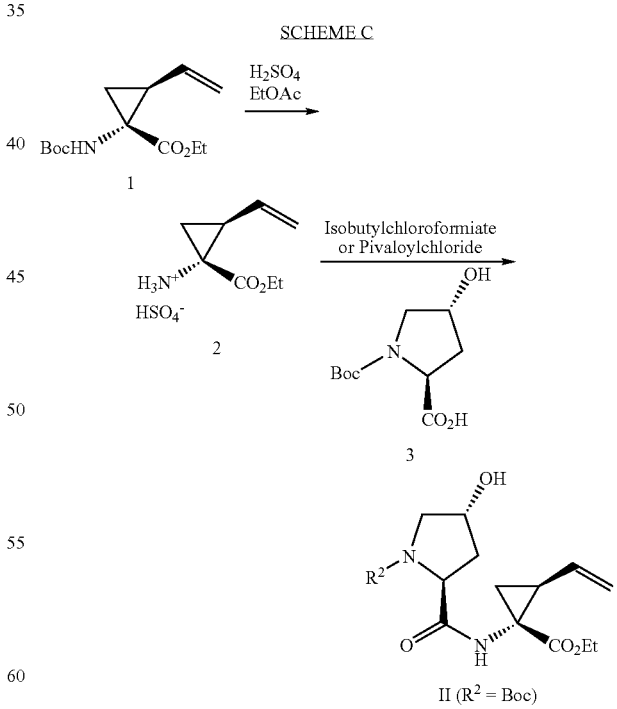

in SCHEME C wherein ethyl vinylcyclopropylcarboxylate 1 is treated with a suitable acid such as sulfuric acid to form 2 and then coupled with 3 and isobutylchloroformate or pivaloyl chloride in the presence of a tertiary amine such as NMM to afford II ($R^2$=Boc). The same reaction sequence, however, with slightly different reaction conditions, is known from the PCT Publication WO 2005/037214.

Step a (SCHEME B) requires the reaction of the dipeptide of the formula II with CDI and with a compound of formula III to form the N-protected carbamate of formula IV wherein $R^2$ preferably is Boc. The compound of formula III can be applied as free base or as a salt formed with a suitable inorganic or organic acid. Preferably a hydrohalogenide salt, more preferably a hydrochloride salt of the compound of formula III is used. A most preferred compound of formula III is the 4-fluoroisoindoline hydrochloride. As a rule the reaction is performed in the presence of an organic solvent. Suitable organic solvents can be selected from polar aprotic solvents and aliphatic or aromatic hydrocarbons. The aromatic hydrocarbon toluene is the preferred solvent.

Step a comprises 2 steps. In a first step the CDI is added and in a second reaction sequence the amine is added to afford the carbamate. For the carbamate formation usually a tertiary amine is present. Suitable tertiary amines are trialkylamines such as TEA or DIPEA, whereby TEA is preferred. The reaction is usually performed at a temperature in the range of −40° C. to 130° C. Usually lower temperatures in the range of 0° C. to 30° C. are required for the CDI addition and slightly higher temperatures in the range of 20° C. to 80° C. are applied for the carbamate formation.

The N-protected carbamate of formula IV can be isolated from the reaction mixture by applying methods known to the skilled in the art such as by extraction with a suitable organic solvent. The N-protected carbamates of formula IV are compounds not known in the prior art and therefore are a further embodiment of the present invention.

In a preferred carbamate of formula IV. Further preferred is the N-protected carbamate of the formula IVb wherein X is fluoro and $R^2$ is Boc.

SCHEME D

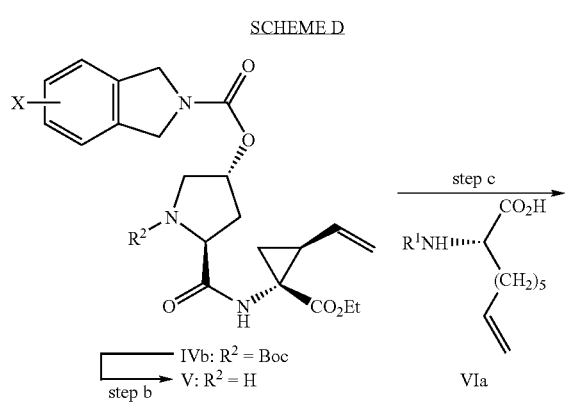

IVb: $R^2$ = Boc
V: $R^2$ = H
step b

Step b (SCHEME D) requires deprotecting the N-protected carbamate of the formula IVb to form the carbamate of formula V. Deprotection can be achieved with an acid in an organic solvent. Suitable acids can be selected from organic acids such as methane- or p-toluene sulfonic acid or inorganic acids such as hydrochloric, hydrobromic or sulfuric acid. Concentrated sulfuric acid is the preferred acid. Suitable organic solvents can be selected from ##DEFN polar protic or aprotic solvents or from aliphatic or aromatic hydrocarbons or mixtures thereof. EtOAc was found to be the preferred solvent. The reaction is usually performed at a temperature in the range of 0° C. to 80° C. The carbamate of formula IVb can be isolated from the reaction mixture by applying methods known to the skilled in the art such as by extraction with a suitable organic solvent. Further purification of the product can be obtained by crystallization of the product in a suitable solvent such as in polar protic or aprotic solvents or from aliphatic or aromatic hydrocarbons or mixtures thereof. Toluene was found to be the preferred solvent.

The carbamates of formula V are compounds not known in the prior art and therefore are a further embodiment of the present invention. A preferred carbamate is a compound of formula V wherein X is fluoro. Further preferred is the carbamate of the formula Vb.

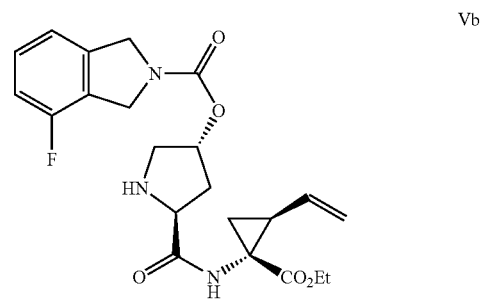

Step c (SCHEME D) requires coupling of the carbamate of formula V with the carboxylic acid of the formula VIa ($R^1$=Boc) or with a salt thereof to form the diene compound of the formula I. The carboxylic acid of formula VIa or the salts thereof are as a rule commercially available. Suitable salts of the carboxylic acid of formula VIa are ammonium salts formed with secondary or tertiary amines such as with dicyclohexylamine or NMM. A tertiary amine such as NMM, TEA or diethylmethylamine, dimethylethylamine, trimethylamine, dimethylpropylamine, diisopropylmethylamine, N,N'-dimethylpiperazine, N-methylpiperidine, preferably NMM or TEA are present. In a preferred embodiment the reaction can be performed without the addition of a tertiary amine.

The reaction is performed in suitable organic solvent which can be selected from polar aprotic solvents or from aliphatic or aromatic hydrocarbons or mixtures thereof such as EtOAc, THF, DMF, DCM, toluene, preferably from EtOAc and or mixtures thereof. The reaction is usually performed at a temperature in the range of −40° C. to 130° C., preferably −40° C. to 60° C. The diene of formula I can be isolated from the reaction mixture by applying methods known to the skilled in the art such as by extraction with a suitable organic solvent, e.g. with toluene.

In a further embodiment the process of the present invention can be used in the preparation of the macrocyclic compound of formula VII wherein X is a halogen atom. In a further embodiment the invention comprises a process for the preparation of the macrocyclic compound of formula VIII.

Commonly used abbreviations include: tert-butoxycarbonyl (Boc), carbonyl diimidazole (CDI), N,N'-dicyclohexylcarbodiimide (DCC), dichloromethane (DCM), di-iso-propylethylamine (DIPEA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), diethyl ether ($Et_2O$), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), iso-propanol (IPA), methanol (MeOH), melting point (mp), methyl (Me), acetonitrile (MeCN), mass spectrum (ms), methyl tert-butyl ether (MTBE), N-methylmorpholine (NMM), N-methylpyrrolidone (NMP), phenyl (Ph), propyl (Pr), iso-propyl (i-Pr), pyridine (pyr), room temperature (rt or RT), satd. (saturated), triethylamine (TEA or Et$_3$N, trifluoroacetic acid (TFA), O-benzotriazol-1-yl-N,N,N',N'-tetramethyluronium tetrafluoroborate (TBTU), tetrahydrofuran (THF), p-toluenesulfonic acid monohydrate (TsOH or pTsOH).

Examples of the processes encompassed by the present invention and within the scope of the invention are provided in the following examples. These examples are provided to enable those skilled in the art to more clearly understand and to practice the present invention. They should not be considered as limiting the scope of the invention, but merely as being illustrative and representative thereof.

EXAMPLE 1

(1R,2S)-1-Amino-2-vinyl-cyclopropanecarboxylic acid ethyl ester

A suspension of 5.11 g (20.0 mmol) of (1R,2S)-1-tert-butoxycarbonylamino-2-vinyl-cyclopropanecarboxylic acid ethyl ester (commercially available from Synthetech Oregon, USA) in 1.94 mL of EtOAc was cooled to 8° C. using an ice bath and a solution of 2.17 g (21.0 mmol) of sulfuric acid in 4.0 mL of EtOAc was added in 5 min. The ice bath was removed and the reaction mixture was stirred for 30 min at RT and 1 h at 50° C. The reaction mixture was then cooled to RT and used in the next step without further purification.

EXAMPLE 2

(2S,4R)-2-((1R,2S)-1-Ethoxycarbonyl-2-vinyl-cyclopropylcarbamoyl)-4-hydroxy-pyrrolidine-1-carboxylic acid tert-butyl ester To a solution of 4.87 g (21.0 mmol) of Boc-(2S,4R)-hydroxyproline in 25 mL of THF 2.03 mL (20.0 mmol) of NMM was added. A suspension was formed. The mixture was cooled to −23° C. and 2.85 g (20.0 mmol) of isobutylchloroformiate was added. After stirring for 10 min additional 4.25 g (42.0 mmol) of NMM was added. To this mixture the solution of (1R,2S)-1-amino-2-vinyl-cyclopropanecarboxylic acid ethyl ester prepared in example 1 was added at a temperature of −15° C. within 5 min. The reaction mixture was stirred for 2.5 h at 0° C. Salts were filtered off and the filtrate was treated with 20 mL of aqueous HCl (0.5 N). The solvents were removed at 50° C. under reduced pressure using a rotary evaporator and the residue was extracted twice with 50 mL of EtOAc. The extract was washed with 40 mL of water and 40 mL of aqueous Na$_2$CO$_3$ solution (10 wt %), and dried over sodium sulfate. Finally the solvent was removed completely to give 8.19 g of (2S,4R)-2-((1R,2S)-1-ethoxycarbonyl-2-vinyl-cyclopropylcarbamoyl)-4-hydroxy-pyrrolidine-1-carboxylic acid tert-butyl ester as a yellow oil. The product was used in the next step without further purification.

EXAMPLE 3

4-Fluoro-1,3-dihydro-isoindole-2-carboxylic acid (3R,5S)-1-tert-butoxycarbonyl-5-((1R,2S)-1-ethoxycarbonyl-2-vinyl-cyclopropylcarbamoyl)-pyrrolidin-3-yl ester To a solution of 8.19 g of crude (2S,4R)-2-((1R,2S)-1-ethoxycarbonyl-2-vinyl-cyclopropylcarbamoyl)-4-hydroxy-pyrrolidine-1-carboxylic acid tert-butyl ester and 60 mL of toluene was added 4.25 g CDI (26.2 mmol) Sin portions at a temperature of 22-25° C. The reaction mixture was stirred for 1.5 h at RT. Then 3.66 g (21.0 mmol) of 4-fluoroisoindoline hydrochloride was added in portions followed by 3.1 mL of TEA. The resulting suspension was heated to 52° C. bath temperature. After stirring for 3 h at this temperature the reaction mixture was cooled with an ice bath and 70 mL of aqueous HCl (1M) were added. The mixture was extracted with 50 mL of toluene. The separated aqueous layer was extracted twice with 50 mL toluene. The combined toluene extracts were washed with 30 mL of water and 30 mL of an aqueous solution of Na$_2$CO$_3$ (5 wt %). The toluene extract was dried (Na$_2$SO$_4$), filtered, and the solvent was completely removed. 9.21 g of 4-fluoro-1,3-dihydro-isoindole-2-carboxylic acid (3R,5S)-1-tert-butoxycarbonyl-5-((1R,2S)-1-ethoxycarbonyl-2-vinyl-cyclopropylcarbamoyl)-pyrrolidin-3-yl ester was obtained as a grey solid, which was used in the next step without further purification.

MS: 532.3 (M$^+$+H). $^1$H-NMR (400 MHz, DMSO-D6, 79.2° C.): 8.40 (s, 1H), 7.37-7.31 (m, 1H), 7.16 (d, J=7.5 Hz, 1H), 7.09-7.05 (m, 1H), 5.73-5.64 (m, 1H), 5.24 (dd, J=17.2, 1.6 Hz, 1H), 5.18 (m, 1H), 5.08 (dd, J=10.4, 1.6 Hz, 1H), 4.67 (m, 4H), 4.22 (t, J=7.7 Hz, 1H), 4.11-4.00 (m, 2H), 3.66 (dd, J=11.9, 4.7 Hz, 1H), 3.54 (d, br, 12.1 Hz, 1H), 2.37-2.28 (m, 1H), 2.19-2.11 (m, 2H), 1.63 (dd, J=7.95, 5.25 Hz, 1H), 1.38 (s, 9H), 1.28 (dd, J=9.4, 5.1 Hz, 1H), 1.16 (t, J=7.0 Hz, 3H).

EXAMPLE 4

4-Fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester A solution of 2.15 g (21.0 mmol) of sulfuric acid in 3.9 mL of EtOAc was added to a suspension of 9.21 g of crude 4-fluoro-1,3-dihydro-isoindole-2-carboxylic acid (3R,5S)-1-tert-butoxycarbonyl-5-((1R,2S)-1-ethoxycarbonyl-2-vinyl-cyclopropyl-carbamoyl)-pyrrolidin-3-yl ester in 31 mL of EtOAc, which was cooled with an ice bath. The ice bath was removed and the reaction mixture was heated to 50° C. for 3 h until all starting material had been consumed. To the reaction mixture an aqueous solution of Na$_2$CO$_3$ (10 wt %) was added. Phases were separated and the aqueous layer was extracted three times with EtOAc. The combine organic extracts were evaporated to dryness and the residue was dissolved in 85 mL of toluene and heated to 102° C. The solution was slowly cooled to 2° C. Crystallization started at 53° C. The crystals were filtered off and dried under reduced pressure to yield 6.62 g (77% over four steps starting from 20.0 mmol (1R,2S)-1-tert-butoxycarbonylamino-2-vinyl-cyclopropanecarboxylic acid ethyl ester; yield not corrected for assay; assay: 97.9% area HPLC) of 4-fluoro-1,3-dihydro-isoindole-2-carboxylic acid (3R,5S)-5-((1R,2S)-1-ethoxycarbonyl-2-vinyl-cyclopropyl-carbamoyl)-pyrrolidin-3-yl ester as grey crystals.

MS: 432.2 (M$^+$+H). $^1$H-NMR (400 MHz, CDCl$_3$): 8.17 (d, J=4.0 Hz, 1H), 7.31-7.25 (m, 1H), 7.08-6.95 (m, 2H), 5.82-5.73 (m, 1H), 5.31 (dd, J=16.4, 1.2 Hz, 1H), 5.29 (m, 1H), 5.13 (dd, J=10.3, 1.7 Hz), 4.82-4.65 (m, 2H), 4.23-4.07 (m, 2H), 3.98 (m, 1H), 3.28 (d, 13.0 Hz, 1H), 3.07-3.02 (m, 1H), 2.46-2.40 (m, 1H), 2.30 (s, br, 1H), 2.26-2.17 (m, 1H), 2.12 (m, 1H), 1.92 (dd, J=7.9, 5.5 Hz, 1H), 1.6-1.56 (m, 1H), 1.24 (t, J=7.1 Hz, 3H).

EXAMPLE 5

4-Fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropylcarbamoyl)-pyrrolidin-3-yl ester A solution of 1.15 g (2.55 mmol) (S)-2-tert-butoxycarbonylamino-non-8-enoic acid dicyclohexylammonium salt (commercially available from Synthetech Oregon, USA) and 469 mg (4.64 mmol) NMM in 9.0 mL of THF was added dropwise to a solution of 302 mg (2.53 mmol) pivaloyl chloride in 1.5 mL of THF while maintaining the temperature at 20-25° C. The suspension was stirred for 45 min, then cooled to 0° C. A solution of 1.00 g (2.32 mmol) of 4-fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester in 13 mL of THF was added to the mixed anhydride at 0° C. The mixture was first stirred for 2.5 h at 2° C., then for 19 h at 26° C. after which 9.5 mL water and 14.8 mL aqueous HCl (0.5 N) were added. The phases were separated and the aqueous layer was extracted with toluene (3×3 mL). The combined organic layers were washed with 2 mL of water, 5 mL of aqueous Na$_2$CO$_3$ (5 wt %) and dried (Na$_2$SO$_4$). The solvent was removed at 50° C. under reduced pressure using a rotary evaporator. The resulting oil was finally dried under oil pump vacuum yielding 1.75 g (88.3%) of 4-fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropylcarbamoyl)-pyrrolidin-3-yl ester as a brown resin with an assay of 80.5 wt %.

EXAMPLE 6

(1R,2S)-1-Amino-2-vinyl-cyclopropanecarboxylic acid ethyl ester

A solution of 153.2 g (600 mmol) of (1R,2S)-1-tert-butoxycarbonylamino-2-vinyl-cyclopropanecarboxylic acid ethyl ester (commercially available from Synthetech Oregon, USA) in 80 mL of EtOAc was dosed to a solution of 65.1 g (630 mmol) of sulfuric acid in 480 mL of EtOAc at 20-25° C. The reaction mixture was stirred for 60 min at 42-48° C. After complete conversion the reaction mixture was cooled to 18-22° C. Then 127.5 g (1260 mmol) of TEA was dosed at 20-30° C. Finally 100 mL of DMF was added. The reaction mixture was used in the next step immediately after preparation.

EXAMPLE 7

(2S,4R)-2-((1R,2S)-1-Ethoxycarbonyl-2-vinyl-cyclopropylcarbamoyl)-4-hydroxy-pyrrolidine-1-carboxylic acid tert-butyl ester To a suspension of 138.8 g (600 mmol) of Boc-(2S,4R)-hydroxyproline in 890 mL of EtOAc was added 63.7 g (630 mmol) of NMM at 20-30° C. To this mixture 72.3 g (600 mmol) of pivaloyl chloride was added at 15-22° C. within 10-20 min followed by 50 mL of EtOAc. The mixture was stirred at 20-25° C. for 60-75 min. Then the emulsion of (1R,2S)-1-amino-2-vinyl-cyclopropanecarboxylic acid ethyl ester prepared in example 6 was added at a temperature of 20-30° C. within 5-30 min. The dosing funnel was rinsed with 20 mL DMF and 100 mL EtOAc. The reaction mixture was stirred for 4 h at 20-25° C. After complete conversion 450 mL of aqueous HCl (lN) was added. Phases were separated and the aqueous layer was extracted with 600 mL of EtOAc. The organic phase was washed with 200 mL of water, 400 mL of aqueous NaOH (2M) and 200 mL of water. The combined organic phases were concentrated to 400 mL under reduced pressure. To the residue 1500 mL of toluene was added and the mixture was concentrated to 1000 mL under reduced pressure. To the residue 720 mL of toluene was added to yield the (2S,4R)-2-((1R,2S)-1-ethoxycarbonyl-2-vinyl-cyclopropylcarbamoyl)-4-hydroxy-pyrrolidine-1-carboxylic acid tert-butyl ester as a 12-13 wt % solution in toluene.

EXAMPLE 8

4-Fluoro-1,3-dihydro-isoindole-2-carboxylic acid (3R,5S)-1-tert-butoxycarbonyl-5-((1R,2S)-1-ethoxycarbonyl-2-vinyl-cyclopropylcarbamoyl)-pyrrolidin-3-yl ester To a solution of (2S,4R)-2-((1R,2S)-1-ethoxycarbonyl-2-vinyl-cyclopropylcarbamoyl)-4-hydroxy-pyrrolidine-1-carboxylic acid tert-butyl ester in toluene (as obtained in example 7) was added 121.1 g CDI (724 mmol, purity 97 wt %) was added in six portions at 20-25° C. After the addition of each portion the reaction mixture was stirred for 20 min. The funnel was rinsed with 100 mL of toluene and the reaction mixture was stirred at 20-25° C. for 1 h. Then 112.5 g (648 mmol) of 4-fluoroisoindoline hydrochloride was added followed by 30.4 g (300 mmol) of TEA and 100 mL of toluene. The resulting suspension was heated to 48-52° C. temperature and stirred at this temperature for 5 h. After the conversion is completed the reaction mixture was heated to 57-62° C. and 546 g of aqueous HCl (2M) was added. The phases were separated and the organic layer was washed with 500 mL of water. The organic phase was then concentrated at a jacket temperature of 60° C. under reduced pressure to a residual volume of 600 mL. To the residue was added 1140 mL of EtOAc. The obtained solution of 4-fluoro-1,3-dihydro-isoindole-2-carboxylic acid (3R,5S)-1-tert-butoxycarbonyl-5-((1R,2S)-1-ethoxycarbonyl-2-vinyl-cyclopropylcarbamoyl)-pyrrolidin-3-yl ester was used in the next step without further purification.

EXAMPLE 9

4-Fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester A solution of 64.4 g (630 mmol) of H$_2$SO$_4$ in 120 mL of EtOAc was added to a suspension of 1.7 L of 4-fluoro-1,3-dihydro-isoindole-2-carboxylic acid (3R,5S)-1-tert-butoxycarbonyl-5-((1R,2S)-1-ethoxycarbonyl-2-vinyl-cyclopropylcarbamoyl)-pyrrolidin-3-yl ester (theoretical amount: 600 mmol; as obtained from example 8) in EtOAc at 50-60° C. The dropping funnel was rinsed with 80 mL of EtOAc and the reaction mixture was stirred for 3 h at 60° C. To the reaction mixture 800 mL of an aqueous solution of Na$_2$CO$_3$ (10 wt %) was added. The phases were separated and the organic layer was washed with 400 mL of water. The organic layer was concentrated at a jacket temperature of 105° C. to a residual volume of 450 mL. To the residue 1000 mL of toluene was added. To initiate crystallization the temperature was decreased to 60° C. and maintained for 30 min at this value. The suspension is cooled to −2° C. and stirred for 1 h at this temperature. The crystals were collected on a suction filter and washed three times with a total of 400 mL of toluene. After drying at 53° C. under reduced pressure there was obtained 198.2 g of 4-fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester as colorless crystals in a purity of 98.0 wt % and a yield of 75% over 4 steps.

EXAMPLE 10

4-Fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropylcarbamoyl)-pyrrolidin-3-yl ester A solution of 57.7 g (128 mmol) (S)-2-tert-butoxycarbonylamino-non-8-enoic acid dicyclohexylammonium salt (commercially available from Synthetech Oregon, USA) in 350 mL of THF was added dropwise to a solution of 15.1 g (125 mmol) pivaloyl chloride in 200 mL of THF while maintaining the temperature at 0-5° C. The dosing funnel was rinsed with 50 mL of THF and the suspension was stirred for 90 min at 5° C. jacket temperature. The temperature was decreased to −5° C. and 50.0 g (116 mmol) of 4-fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester was added in five portions within 30 min to the mixed anhydride at −5° C. to 0° C. The funnel was rinsed with 25 mL of THF. The suspension was first stirred for 30 min at 0° C., then for 6 h at 23° C. After complete conversion 150 mL of water was added. The reaction mixture was concentrated at 50° C. jacket temperature under reduced pressure to a residual volume of 300 mL. After cooling to 23° C. 500 mL of toluene and 58 mL of aqueous HCl (1M) were added. The suspension was filtered and the reaction vessel and filter cake were washed with 220 mL of toluene. The phases of the filtrate were separated and the aqueous layer was extracted with 150 mL of toluene. The organic layers were washed separately with 200 mL of aqueous $Na_2CO_3$ (10 wt %) and 58 mL of aqueous HCl (1M). The combined organic layers were concentrated at 50° C. under reduced pressure using a rotary evaporator to afford 143.3 g of crude (54.5 wt %) 4-fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropyl-carbamoyl)-pyrrolidin-3-yl ester in a yield of 98.4%.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof. The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:
1. A process for preparing a diene of formula I wherein:

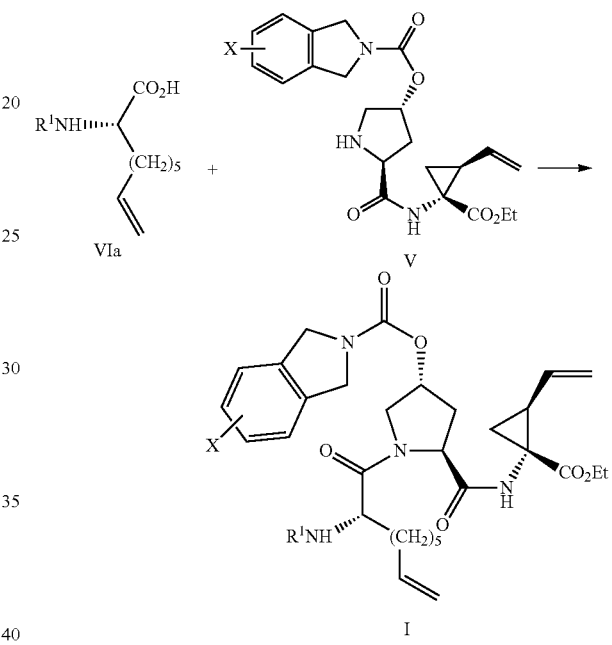

$R^1$ is an amino protecting group and X is a halogen atom comprising the coupling of the carboxylic acid of formula VIa or a salt thereof and the dipeptide V.

2. A process according to claim 1 wherein the coupling is carried out with a coupling agent selected from the group consisting of alkyl chloroformates, carboxylic acid halogenides and carbodiimides in the presence of a tertiary amine.

3. A process according to claim 2 wherein said coupling agent is isobutyl choroformate or pivaloyl chloride and said tertiary amine is N-methylmorpholine or triethylamine.

4. A process according to claim 1 wherein X is fluorine.

5. A process according to claim 1 which process further comprises the steps of:

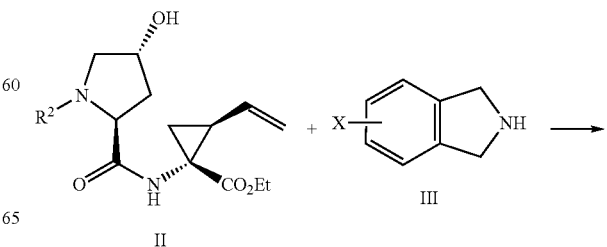

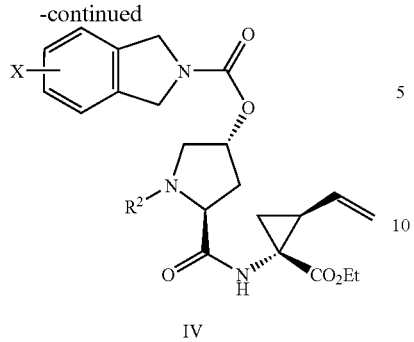

IV (a) reacting a dipeptide of formula II wherein $R^2$ is an amino protecting group with carbonyl diimidazole and a compound according to formula III wherein X is a halogen and III is a free base or a salt thereof to form an N-protected carbamate of the formula IV;
(b) deprotecting the N-protected carbamate to form a compound of formula V wherein X is as above; and
(c) coupling the carbamate of formula V with the carboxylic acid of formula VIa or with a salt thereof to form the diene of formula I.

6. A process according to claim 5 wherein X is fluoride and $R^1$ and $R^2$ are a Boc protecting group.

7. A process according to claim 5 wherein said diene is a compound of formula Ib

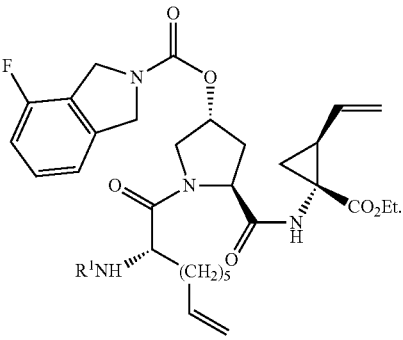

Ib

8. A process according to claim 5 wherein step (a) is carried out in the presence of a tertiary amine base and an organic solvent.

9. A process according to claim 5 wherein the deprotection of the N-protected carbamate of formula IV in step (b) is performed with an acid in an organic solvent.

* * * * *